United States Patent
Janzig et al.

(10) Patent No.: US 10,632,316 B2
(45) Date of Patent: Apr. 28, 2020

(54) ELECTRICAL CONTACT FOR IMPLANTABLE MEDICAL DEVICE

(71) Applicant: Medtronic, Inc., Minneapolis, MN (US)

(72) Inventors: Darren A. Janzig, Center City, MN (US); Chris J. Paidosh, St. Anthony, MN (US); Paulette C. Olson, Eagan, MN (US); Gerald G. Lindner, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 147 days.

(21) Appl. No.: 15/624,202

(22) Filed: Jun. 15, 2017

(65) Prior Publication Data
US 2017/0281951 A1 Oct. 5, 2017

Related U.S. Application Data

(60) Division of application No. 14/790,171, filed on Jul. 2, 2015, now Pat. No. 9,687,660, which is a
(Continued)

(51) Int. Cl.
*H01R 43/20* (2006.01)
*A61N 1/375* (2006.01)
(Continued)

(52) U.S. Cl.
CPC .......... *A61N 1/3752* (2013.01); *H01R 13/111* (2013.01); *H01R 13/42* (2013.01);
(Continued)

(58) Field of Classification Search
CPC ...... A61N 1/3752; H01R 43/16; H01R 43/02; H01R 13/5202; H01R 13/42; H01R 24/58;
(Continued)

(56) References Cited

U.S. PATENT DOCUMENTS

| | | |
|---|---|---|
| 4,898,173 A | 2/1990 | Daglow et al. |
| 4,995,389 A | 2/1991 | Harris |

(Continued)

*Primary Examiner* — Donghai D Nguyen
(74) *Attorney, Agent, or Firm* — Mueting, Raasch and Gebhardt, P.A.

(57) ABSTRACT

A one-piece electrical contact ring for use in a lead receptacle of an implantable medical device includes (i) a tubular body defining a cavity extending through the body and (ii) a plurality of resiliently deflectable elements extending from the tubular body into the cavity. The deflectable elements have a lead contacting portion configured to contact the lead when received by the cavity. The lead contacting portions of the deflectable elements in a relaxed state are located in a plane that intersects the tubular body and are configured to deflect along the plane towards the tubular body as the lead is inserted in the contact ring. The contact ring may further include a plurality of stops, each configured to (i) engage a stop portion of the elements when the elements are sufficiently outwardly deflected and (ii) inhibit further outward deflection of the elements when the stops engage the stop portions.

8 Claims, 13 Drawing Sheets

Related U.S. Application Data continuation of application No. 12/555,431, filed on Sep. 8, 2009, now Pat. No. 9,095,728.

(60) Provisional application No. 61/094,499, filed on Sep. 5, 2008.

(51) Int. Cl.

| | | |
|---|---|---|
| *H01R 13/11* | (2006.01) | |
| *H01R 24/58* | (2011.01) | |
| *H01R 13/42* | (2006.01) | |
| *H01R 13/52* | (2006.01) | |
| *H01R 43/02* | (2006.01) | |
| *H01R 43/16* | (2006.01) | |
| *H01R 107/00* | (2006.01) | |

(52) U.S. Cl.
CPC ......... *H01R 13/5202* (2013.01); *H01R 24/58* (2013.01); *H01R 43/02* (2013.01); *H01R 43/16* (2013.01); *H01R 2107/00* (2013.01); *Y10T 29/4921* (2015.01)

(58) Field of Classification Search
CPC .............. H01R 13/111; H01R 2107/00; Y10T 29/49204; Y10T 29/49208; Y10T 29/49211

USPC ...... 29/874, 876, 878; 439/349, 909; 607/37
See application file for complete search history.

(56) References Cited

U.S. PATENT DOCUMENTS

| | | | |
|---|---|---|---|
| 5,730,628 A | | 3/1998 | Hawkins |
| 5,766,042 A | * | 6/1998 | Ries ..................... A61N 1/056 |
| | | | 439/349 |
| 7,003,351 B2 | * | 2/2006 | Tvaska ................. A61N 1/375 |
| | | | 439/909 |
| 7,167,749 B2 | | 1/2007 | Biggs et al. |
| 7,402,083 B2 | | 7/2008 | Kast et al. |
| 7,711,428 B2 | | 5/2010 | Janzig et al. |
| 7,822,477 B2 | * | 10/2010 | Rey ..................... A61N 1/3752 |
| | | | 607/37 |
| 2004/0167582 A1 | | 8/2004 | Tvaska et al. |
| 2005/0027327 A1 | | 2/2005 | Ries et al. |
| 2005/0107859 A1 | | 5/2005 | Daglow et al. |
| 2006/0004419 A1 | | 1/2006 | Olbertz |
| 2006/0047322 A1 | | 3/2006 | Naviaux |
| 2006/0095086 A1 | | 5/2006 | Balsells |

\* cited by examiner

ELECTRICAL CONTACT FOR IMPLANTABLE MEDICAL DEVICE

CROSS REFERENCE TO RELATED APPLICATIONS

This application is a divisional of U.S. patent application Ser. No. 14/790,171, filed on Jul. 2, 2015 and which will issue as U.S. Pat. No. 9,687,660; which is a continuation of U.S. patent application Ser. No. 12/555,431, filed on Sep. 8, 2009 and issued as U.S. Pat. No. 9,095,728; which claims the benefit of U.S. Provisional Patent Application Ser. No. 61/094,499 filed Sep. 5, 2008, which applications are each hereby incorporated herein by reference in their entries to the extent that it does not conflict with the disclosure presented herein.

FIELD

This application relates to medical devices, more particularly to implantable medical devices operably countable to leads or lead extensions and to electrical contact assemblies for operably coupling the leads to the devices.

BACKGROUND

Implantable electrical signal generators, such as pacemakers, defibrillators, neurostimulators, and the like, have been used to treat a variety of diseases. Such devices generate electrical signals that are transferred to a patient's tissue through electrodes disposed on a distal end portion of a lead. The proximal end portion of a lead typically contains a number of connector rings corresponding to the number of electrodes. Conductors run within and along the lead body and electrically couple the connectors to the electrodes. The proximal end portion of the lead is inserted into lead receptacle of a signal generator such that electrical contact is made between discrete contacts in the receptacle and the connector rings of the lead. The contacts of the receptacle typically include a garter spring within a ferrule. The ferrule is typically electrically coupled to a feedthrough that provides electrical coupling with electronics of the device. The garter spring contacts a contact ring of a lead, electrically coupling the lead to the device electronics via the ferrule and feedthrough. While such lead receptacle contacts have been proven to perform very well over time, garter rings are difficult to manufacture and must provide two contacts for proper electrical connection: one contact with the lead connector ring, and the other with the ferrule. Further, because of the spring configuration, the spring contacts the lead connector ring and the ferrule at multiple points, with each separate contact resulting in increased electrical resistance. Such resistance could result in undesirably large power consumption.

BRIEF SUMMARY

One-piece conductive contacts that may be used in lead receptacles of implantable medical devices are described herein. For example, a one-piece electrical contact ring for use in a lead receptacle of an implantable medical device includes a tubular body defining a cavity extending through the body. The cavity is configured to receive a lead. The one-piece contact ring further includes a plurality of resiliently deflectable elements extending from the tubular body into the cavity. The deflectable elements have a lead contacting portion configured to contact the lead when the lead is received by the cavity. The lead contacting portions of the deflectable elements in a relaxed state are located in a plane that intersects the tubular body and are configured to deflect along the plane towards the tubular body as the lead is inserted in the contact ring In various embodiments, the contact ring further includes a plurality of stops, each configured to (i) engage a stop portion of the elements when the elements are sufficiently outwardly deflected and (ii) inhibit further outward deflection of the elements when the stops engage the stop portions.

By employing a one-piece contact ring for a lead receptacle of an implantable medical device, the complexity of assembly of the device is reduced. Further, the number of electrical contacts required to electrically couple the lead to electronics of the device is reduced; i.e., by eliminating the garter spring one less contact is needed with the one-piece contact rings described herein, which may reduce electrical resistance and power consumption. The number of points of contact between the ring contact and lead may also be reduced relative to a garter spring, further reducing potential sources for electrical resistance. In addition, contact rings described herein may be made according to a number of readily available manufacturing techniques. Many of the rings described herein should be readily scalable. These and other advantages will be readily understood from the following detailed descriptions when read in conjunction with the accompanying drawings.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "active implantable electrical device" or the like refers to a device that is capable of generating, sending or receiving an electrical signal via a medical lead.

As used herein, "tubular" means having the shape and configuration of a tube. "Tube", as used herein means a hollow object having a body and a cavity extending through the body. A tube may take any suitable shape, such as a cylinder, a cuboid, or the like.

The present disclosure relates to contact rings for lead receptacles of implantable medical devices. The electrical contact rings described herein are one-piece. Such one-piece contacts may result in improved reliability due to decreased number of required contacts, simplified assembly, and ease of manufacturability.

Figure 1:
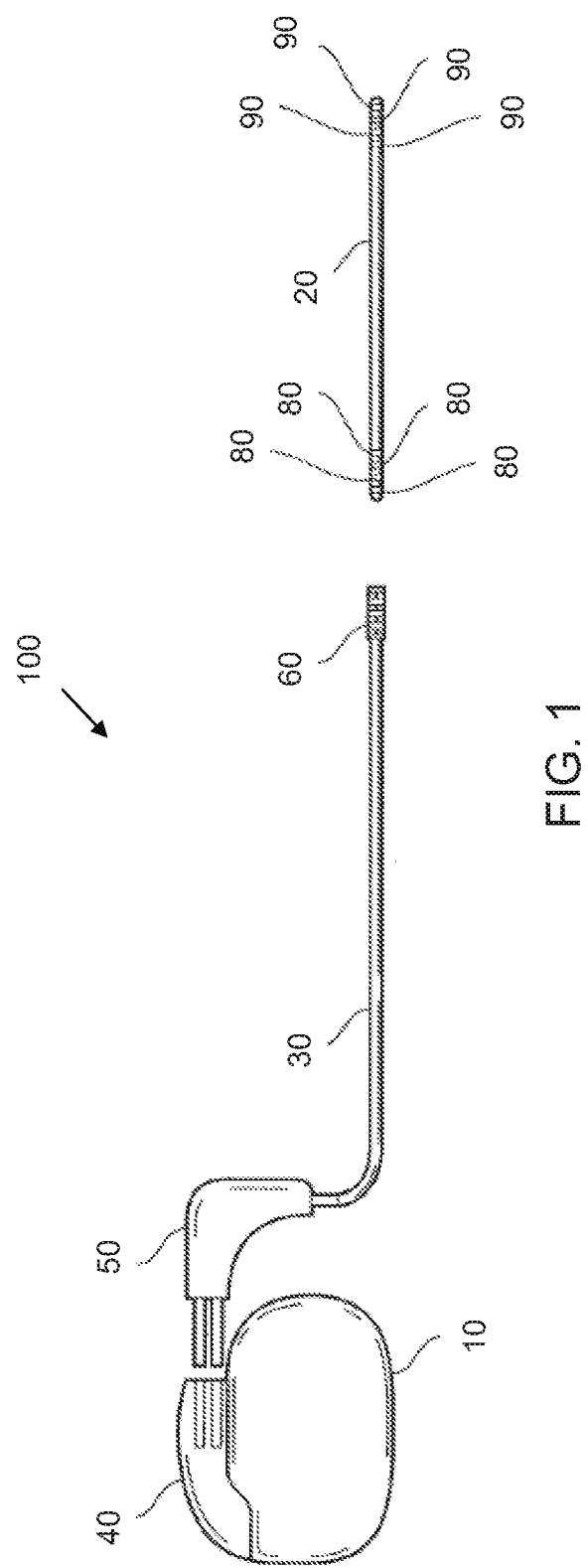
FIG. 1 is a schematic diagram of an exploded view of a representative implantable active electrical device and associated lead and extension.

Referring to FIG. 1, a schematic of an exploded view of a representative implantable medical device system 100 in which such one-piece contact rings may be employed is shown. The system 100 includes an implantable active electrical device 10, and a lead 20 operably couplable to active electrical device 10. Active electrical device 10 may be any electrical signal generator or receiver useful for delivering therapy to a patient or for patient diagnostics. For example, active electrical device 10 may be a hearing implant; a cochlear implant; a sensing or monitoring device; a signal generator such as a cardiac pacemaker or defibrillator, a neurostimulator (such as a spinal cord stimulator, a brain or deep brain stimulator, a peripheral nerve stimulator, a vagal nerve stimulator, an occipital nerve stimulator, a subcutaneous stimulator, etc.), a gastric stimulator; or the like. As shown in FIG. 1, the system 100 may include a lead extension 30 or other adaptor to couple lead 20 to active electrical device 10. While not shown, it will be understood that more than one lead 20 may be operably coupled to one active electrical device 10 or one extension 30 or that more than one extension 30 may be operably coupled to one active electrical device 10. It will also be understood that lead 20 may be coupled to active electrical device 10 without extension 30 or adaptor.

Active electrical device 10 may include a connector header 40 for connecting to lead 20 or extension 30 or other adaptor to couple lead 20 to active electrical device 10. In the embodiment depicted in FIG. 1, the connector header 40 is configured to receive a proximal connector portion 50 of a lead extension 30. The extension 30 includes a distal connector 60 configured to receive proximal end of lead 20. Distal connector 60 has internal electrical contacts 70 configured to electrically couple extension 30 to lead 20 via electrical contacts 80 disposed on the proximal end portion of lead 20. Electrodes 90 are disposed on distal end portion of lead 20 and are electrically coupled to electrical contacts 80, typically through conductors (not shown) within the body of the lead 20. Lead 20 may include any number of electrodes 90, e.g. one, two, three, four, five, six, seven, eight, sixteen, thirty-two, or sixty-four. Typically, each electrode 90 is electrically coupled to a discrete electrical contact 80.

Figure 2:
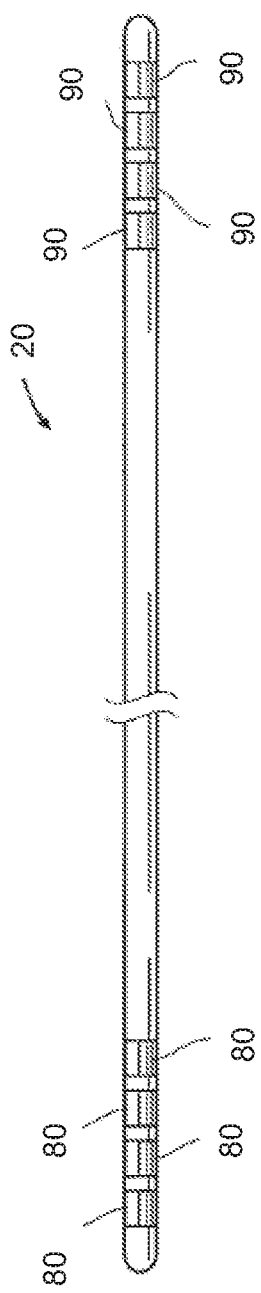
FIG. 2 is a schematic diagram of a perspective view of a representative lead.
Figure 3:
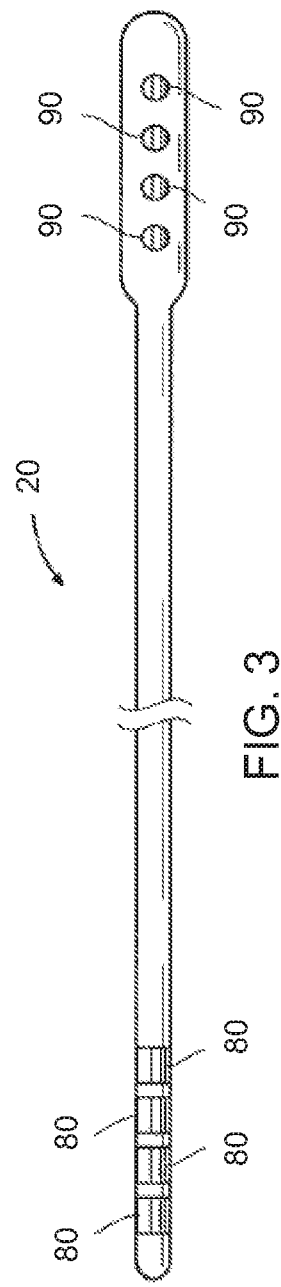
FIG. 3 is a schematic diagram of a perspective view of a representative lead.

FIGS. 2 and 3 are schematic perspective views of representative leads 20. Leads 20, as shown in FIGS. 2 and 3, contain four exposed electrical contacts 80 and four electrodes 90. However, it will be understood that a lead 20 may include any number of contacts 80 or electrodes 90, such as 1, 2, 3, 4, 8, 16, 32, or 64. The contacts 80 are typically electrically coupled to the electrode 90 via conductors (not shown) running within the lead body. Typically each contact 80 is operably coupled to a discrete contact in an active electrical medical device such that a discrete electrical signal may be applied to each electrode 90 or electrode pair. The lead contacts 80 may be electrically coupled to the device via direct insertion into a receptacle of the device or via an extension or adaptor (see, e.g., FIG. 1). The lead 20 shown in FIG. 3 is a paddle-type lead. However, it will be understood that any lead configuration may be employed in accordance with the teachings provided herein.

Figure 4:
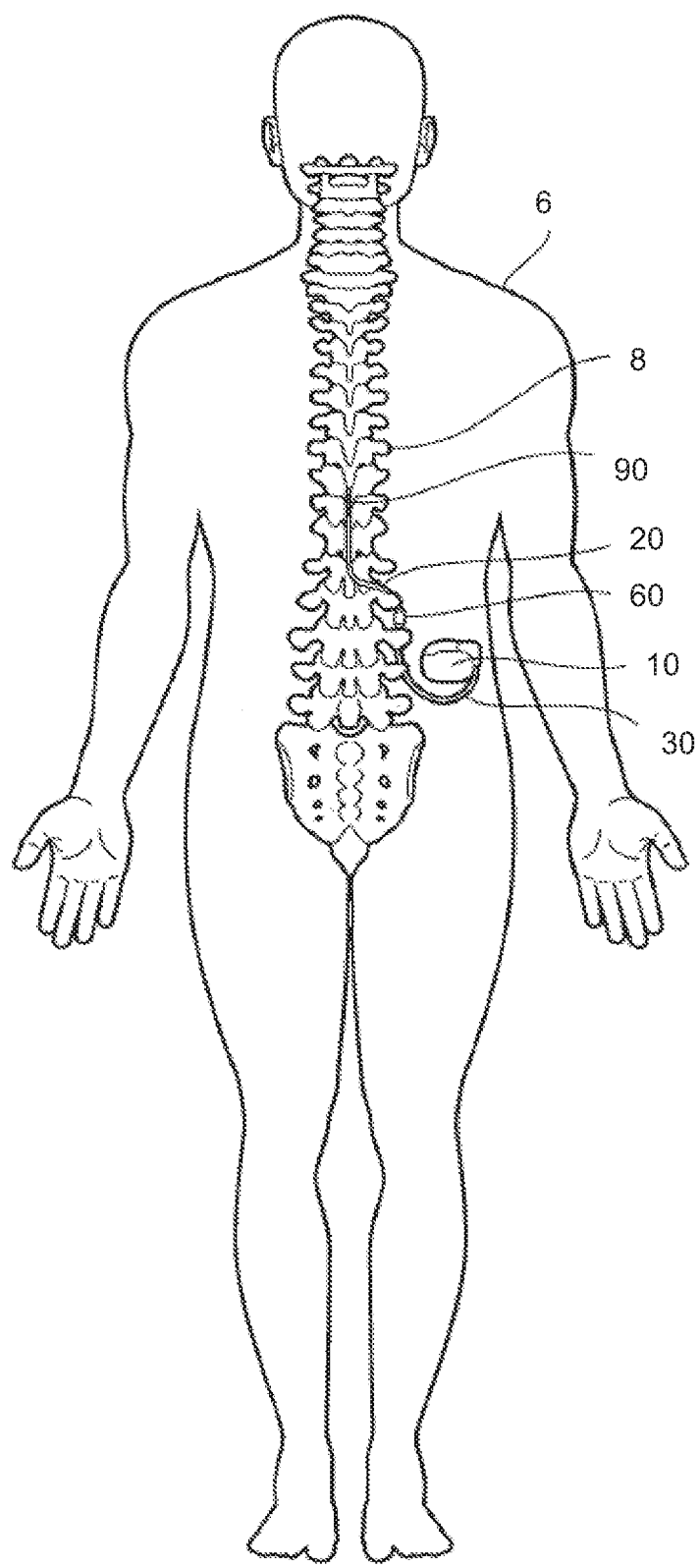
FIG. 4 is a schematic diagram of a representative spinal cord stimulation (SCS) system implanted in a patient.

By way of example and referring to FIG. 4, a spinal cord stimulation (SCS) system, is shown implanted in a patient 6. For SCS, an electrical signal generator 10 is typically placed in a medically appropriate location of the patient 6, such as in the abdominal or pectoral region, and distal portion of lead 20 containing electrodes 90 is placed at a desired location along spinal cord 8. The proximal portion of lead 20 is connected to distal connector 60 of lead extension 30, which is connected to device 10. Such a system, or any system including an electrical signal generator 10 as described herein, may also include an external programmer (not shown), such as a physician programmer or a patient programmer, for telemetric communication with the electrical signal generator 10. Electrical signal generator 10 is capable of generating electrical signals that may be applied to tissue of patient 6 via electrodes 90 for therapeutic or diagnostic purposes. Electrical signal generator 10 contains a power source and electronics for sending electrical signals to the spinal cord 8 via electrodes 90 to provide a desired therapeutic effect. It will be appreciated that other systems employing active electrical devices and therapeutic uses thereof are contemplated.

For the purposes of the remainder of this disclosure, "lead" and "lead extension" are used interchangeably.

Figure 5A:
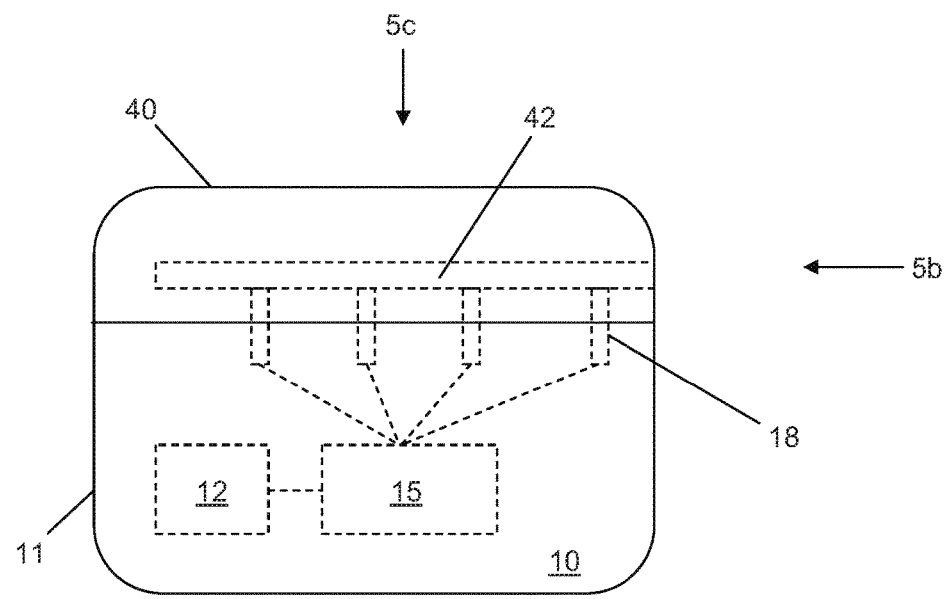
FIG. 5A is a schematic diagram of a side view of an active implantable medical device with representative internal components shown in dashed lines.

Referring now to FIG. 5A, a schematic side view of a representative active implantable electrical device 10 is shown, with selected internal components shown in dashed lines. The device 10 includes a header 40 having a lead receptacle 42 extending therein. The lead receptacle 42 is configured to receive a proximal portion of a lead, extension or adaptor. The receptacle 42 includes one or more electrically conductive portions (not shown) configured to electrically couple with proximal contacts 80 of a lead 20 (see, e.g., FIGS. 2-3) or lead extension. The conductive portions are electrically coupled to electronics 15 disposed within hermetically sealed device housing 11. Hermetically sealed electrical feedthroughs 18 may be used to couple conductive portions of the receptacle 42 to the electronics 15. In the depicted embodiment, the electronics 15 are operably coupled to a power source 12, such as a battery, capacitor, or the like. The header 40 may be attached to hermetically sealed housing 11 of device 10 by, for example, fasteners, adhesives, welds, or the like.

In some embodiments (not shown), the lead receptacle 42 extends within hermetically sealed housing 11. In such embodiments, device 10 may not include a header 40 and feedthroughs 18. Any suitable hermetically sealed receptacle may be employed in such embodiments, such as those described in U.S. patent application Ser. No. 11/733,247, filed on Apr. 10, 2007, entitled "Hermetic Lead Connector Assembly", which application is hereby incorporated herein by reference in its entirety to the extent that it does not conflict with the disclosure presented herein.

Figure 5B:
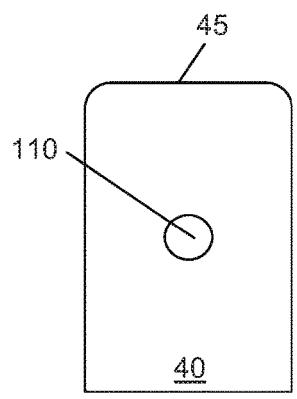
FIG. 5B is a schematic diagram of a front view of the device depicted in FIG. 5A viewed along line 5b of FIG. 5A.
Figure 5C:
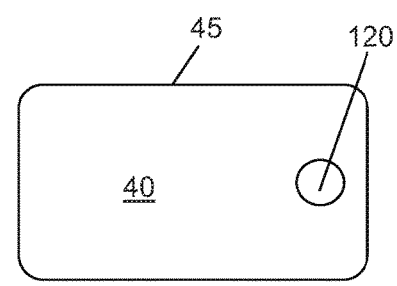
FIG. 5C is a schematic diagram of a top view of the device depicted in FIG. 5A viewed along line 5c of FIG. 5A.

Referring now to FIG. 5B, a schematic front view of the header 40 along line 5b in FIG. 5A is shown. An opening 110 of the lead receptacle is formed in housing 15. In FIG. 5C, a top view of the header 40 along line 5c in FIG. 5A is shown. The housing 45 of header 40 defines an opening 120 for receiving a set screw for assisting in retaining a lead in the receptacle.

Figure 5D:
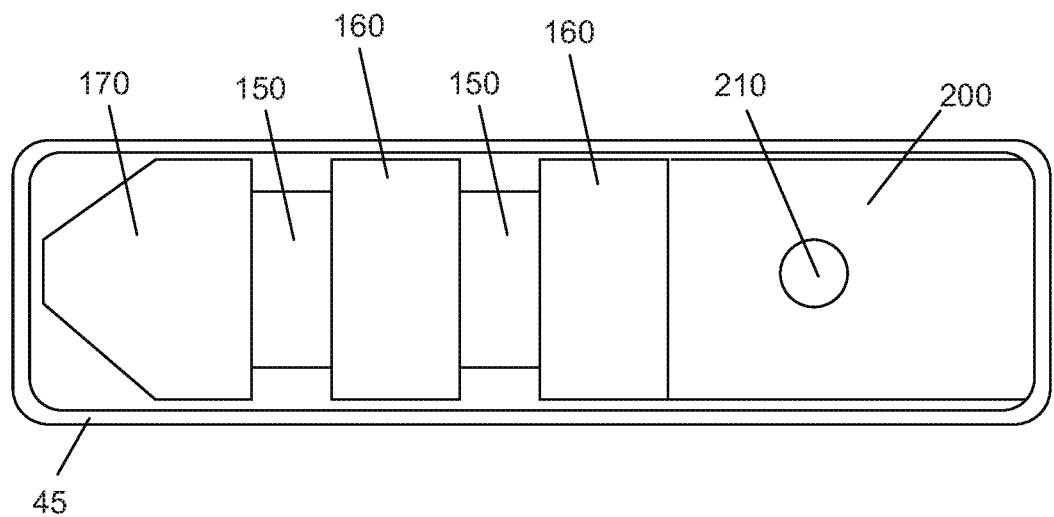
FIG. 5D is a schematic diagram of a cut away top view of the device depicted in FIG. 5A.
Figure 5E:
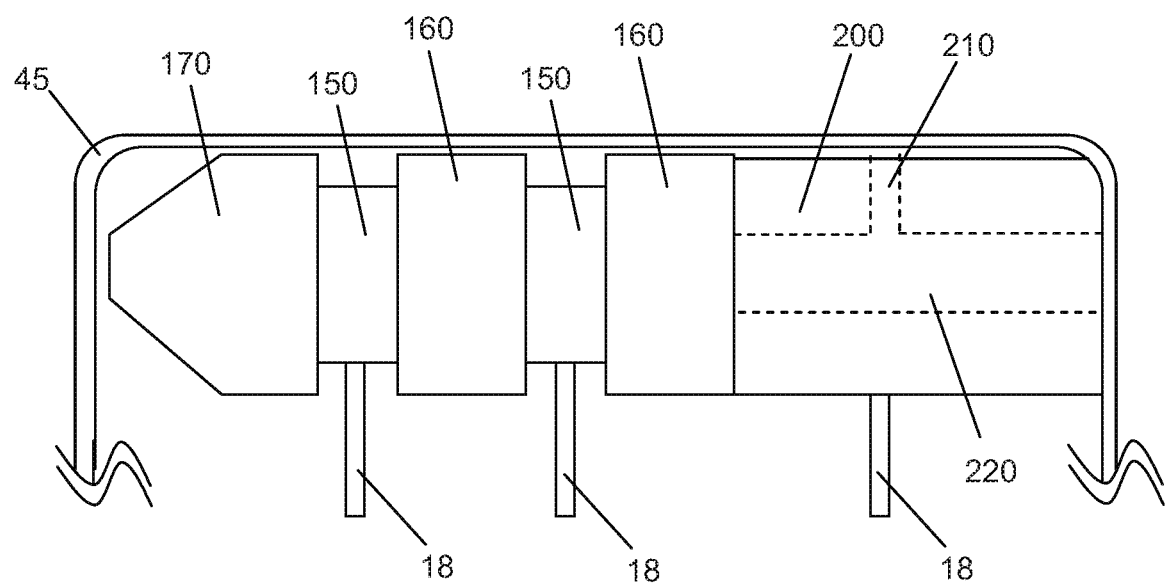
FIG. 5E is a schematic cut away side view of an alternative embodiment of the device depicted in FIG. 5A with representative internal components shown in dashed lines.

In FIGS. 5D-E, schematics of a cut away top view (5E) and a cut away side view (5F) of an embodiment of a header 40 of FIG. 5A are shown. In the depicted embodiment, exterior portions of the lead receptacle are shown. In FIG. 5E, dashed lines represent bores 210, 220 formed in set screw block 200. The receptacle includes alternating conductive 150 and insulating 160 sections. The conductive sections 150 are positioned such that when a lead is inserted into the receptacle, a contact on proximal portion may be electrically coupled with a conductive section 150. The conductive sections 150 of the receptacle are electrically coupled to feedthroughs 18 that couple the conductive sections 150 to electronics of the device. Set screw block 200 of the receptacle may be fixed relative to housing 45. The lead receptacle may include an end cap 170. End cap 170 may fit snuggly against housing 45 or other feature such that an axially compressive force is applied to the receptacle.

Set screw block 200 defines a lead receiving bore 220 and a second bore 210 configured to receive a set screw. The second bore 210 is generally perpendicular to and intersects with the lead receiving bore 220. In the depicted embodiment, set screw block 200 is conductive and is electrically coupled to a feedthrough 18 that serves to electrically couple the block 200 to electronics of the device.

While the lead receptacle depicted in FIGS. 5C-E, include a set screw block, it will be understood that any mechanism for retaining a lead other than a set screw may be employed. It will also be understood that the lead receptacles described herein are applicable to devices having headers that are not fully enclosed by a housing. Such headers are well known and are typically open-faced. Lead receptacles are typically sealed to such header housings with medical adhesive and are back-filled with medical polymeric material, such as silicone, to provide a seal between the electrically conductive portions of the lead receptacle and tissue or fluid of a patient when implanted.

Figure 6:
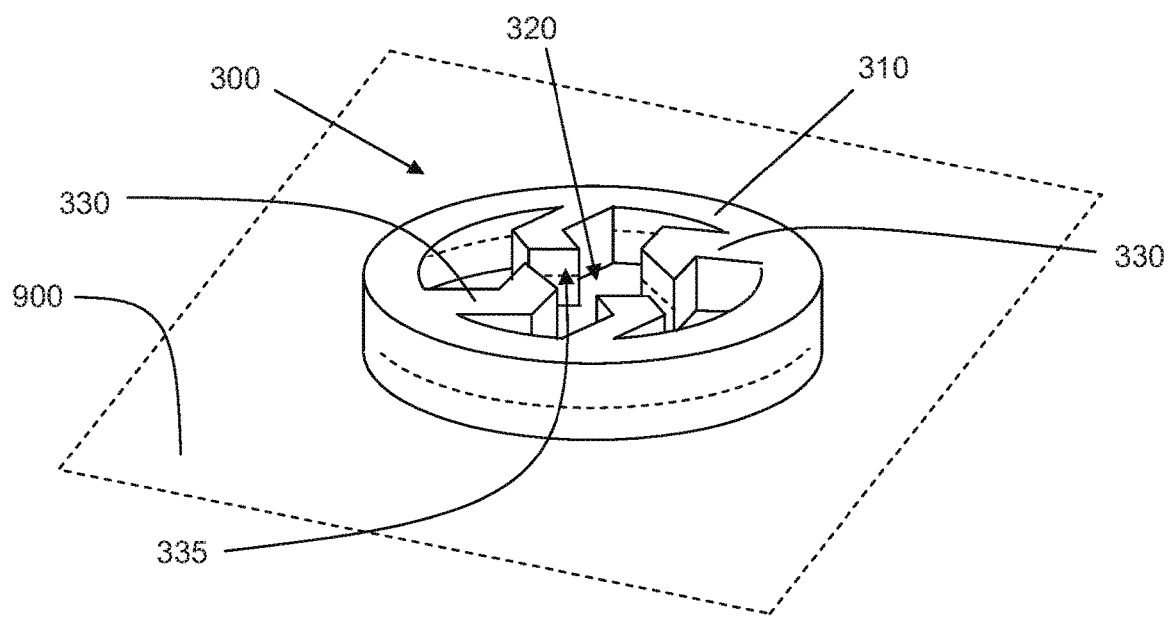
FIGS. 6-7 are schematic diagrams of perspective views of embodiments of electrical contact rings.
Figure 7:
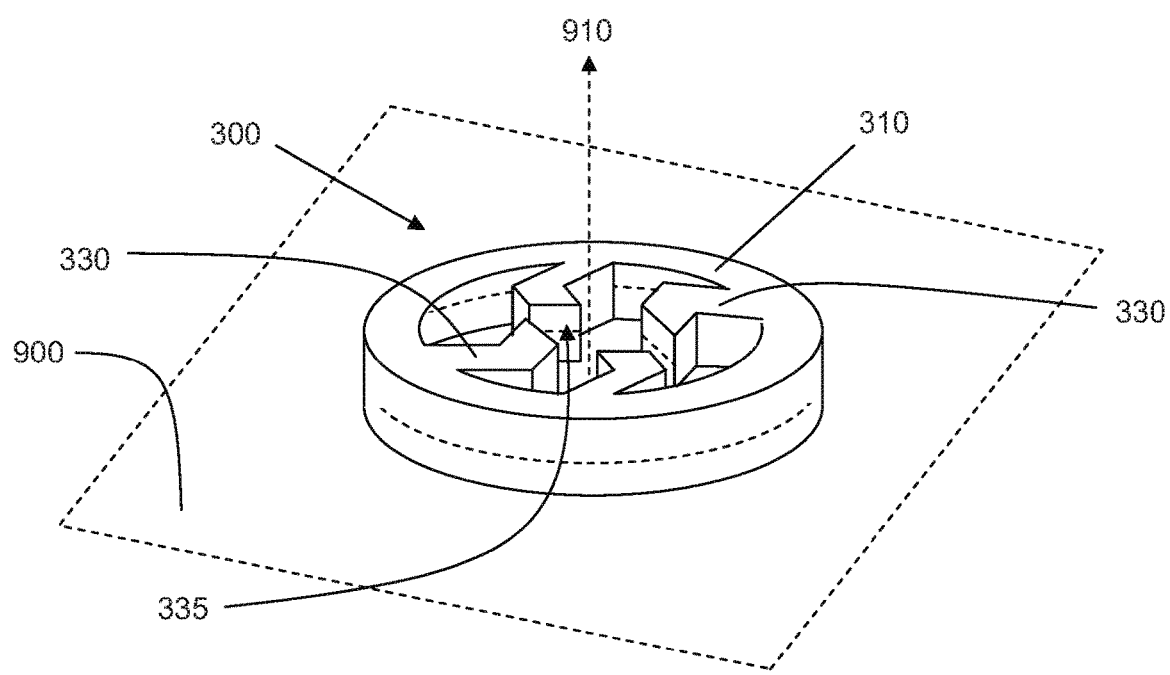

Referring now to FIGS. 6-7, representative embodiments of one-piece electrical connector contact rings 300 that may serve as conductive portions 150 (see, e.g., FIGS. 5D-E) of a lead receptacle are shown. The depicted contact rings 300 include a tubular body 310 defining a cavity 320 extending through the body 310. The cavity 320 is configured to receive a lead. The contact ring 300 includes a plurality resiliently deflectable elements 330. The deflectable elements 330 have lead contacting portions 335 configured to contact a contact of a lead when the lead is inserted into the cavity 320. The lead contacting portions 335 of the deflectable elements 330, in a relaxed state, are located in a plane 900 that intersects the tubular body 310. The lead contacting portions 335 are configured to deflect along the plane 900 towards the tubular body 320 as the lead is inserted in the cavity 320. As shown in FIG. 7, the plane 900 may be orthogonal to the central axis 910 of the cavity 320. The dashed lines on the tubular body 310 and contacting portions 335 of the deflectable elements 330 shown in FIGS. 6-7 depict the location of intersection of the plane 900.

Figure 8A:
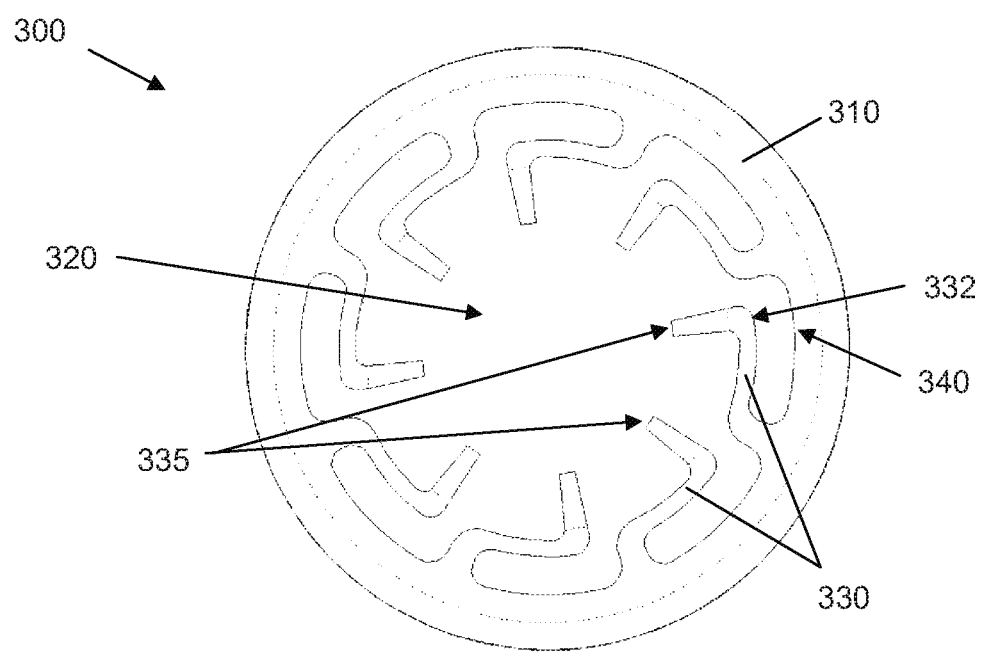
FIGS. 8A-D and 8F are schematic drawings of front or perspective views of representative embodiments electrical contact rings according to various embodiments.

Referring now to FIGS. 8A-F, representative embodiments of one-piece electrical connector contact rings 300 are shown. The contact rings 300 depicted in FIG. 8A are configured to operate in a manner similar to the ring described with regards to FIG. 6 or FIG. 7. That is, the rings 300 include tubular bodies 310 defining a cavity 310 a plurality of resiliently deflectable members 320 extending from the tubular body and having lead contacting portions 335, where the lead contacting portions 335 lie in a plane that intersects the tubular body 310 and where the contacting portions 335 are configured to deflect along the plane towards the tubular body 310 when the lead is inserted into the cavity 320. In the embodiments depicted in FIGS. 8A-F, the deflectable members 330 extend into the cavity 320 in a non-radial manner (in a direction not along a radius). As a lead is inserted into the cavity 320 of contact 300, elements 330 deflect outwardly (relative to axial center of contact 300) in a non-radial manner in the depicted embodiments. While portions of the elements 330, such as lead contacting portion 335, may deflect outwardly in a radial manner, the overall element 310 is configured to deflect non-radially when a lead is inserted. That is, the sum total of vectors of deflection along the length of an element 330 is non-radial. As used herein, "non-radial" with regard to outward deflection means deflection in a direction other than along a line defined by a radius.

Figure 8B:
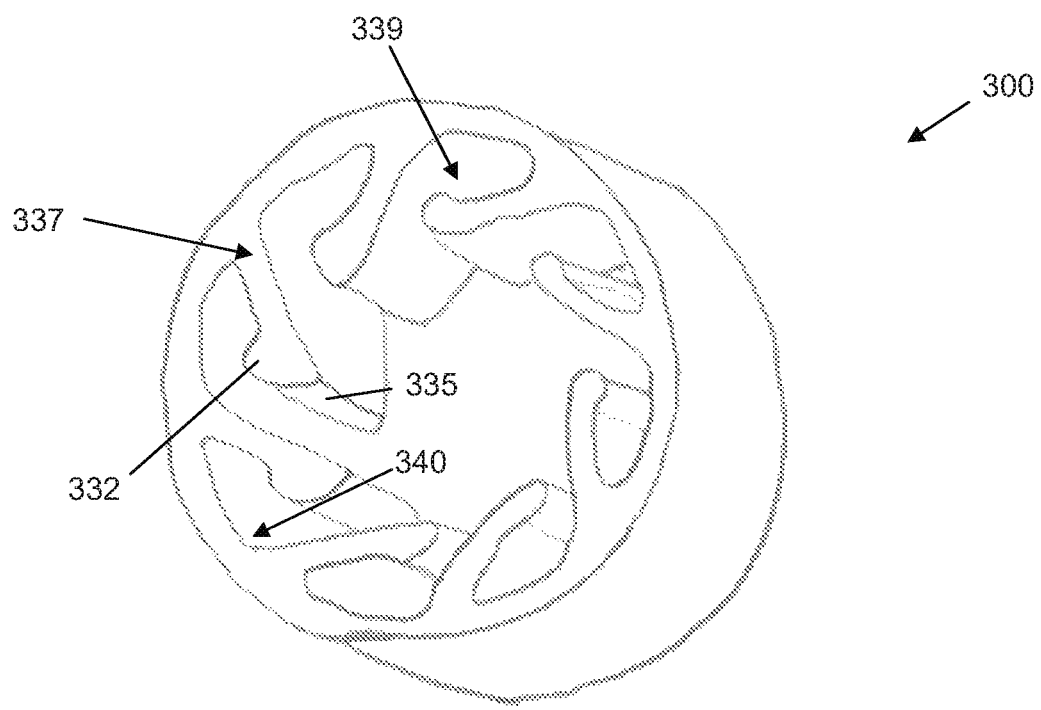
Figure 8C:
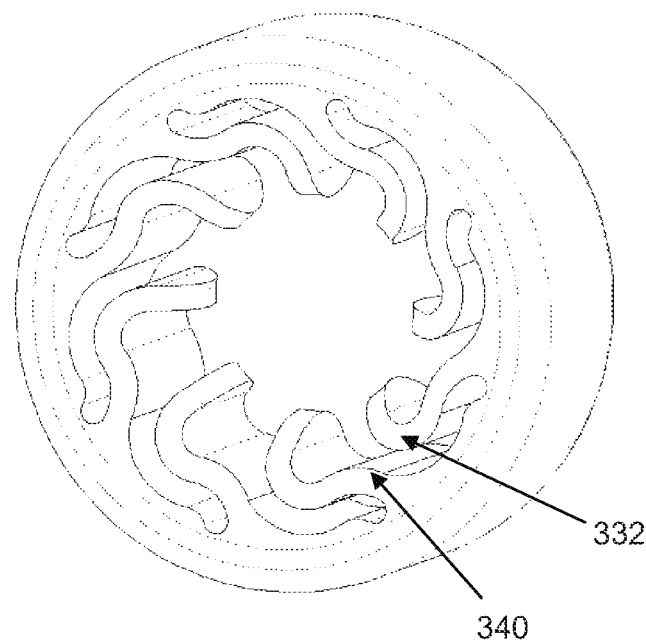
Figure 8D:
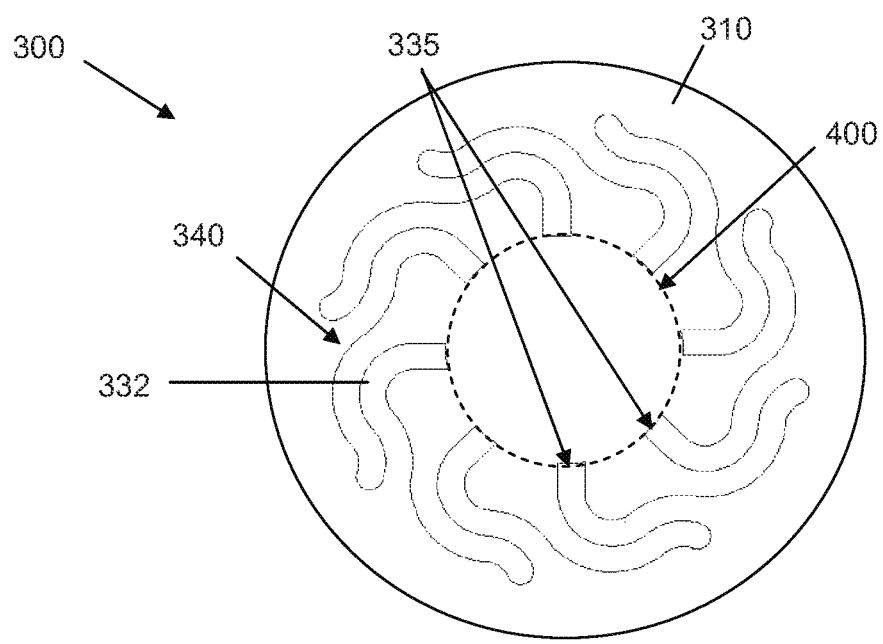
Figure 8E:
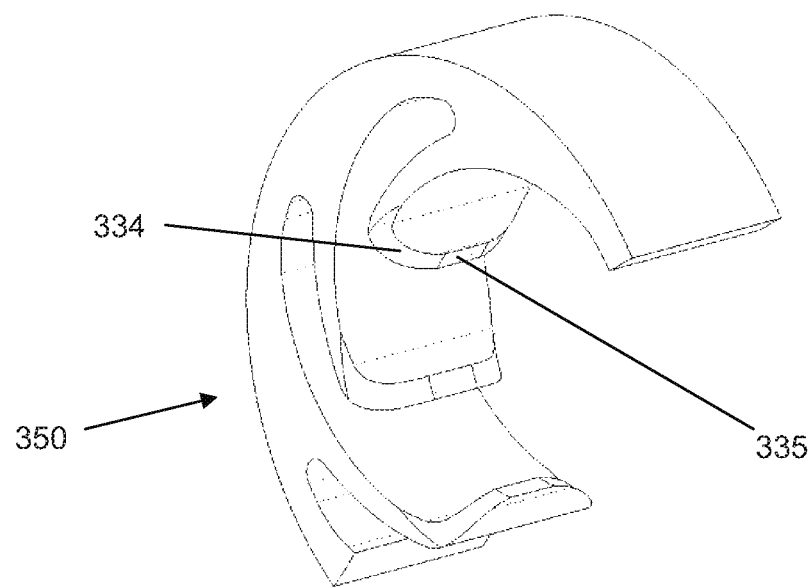
FIG. 8E is a schematic drawing of a cut away perspective view of a portion of the contact ring depicted in FIG. 8F.
Figure 8F:
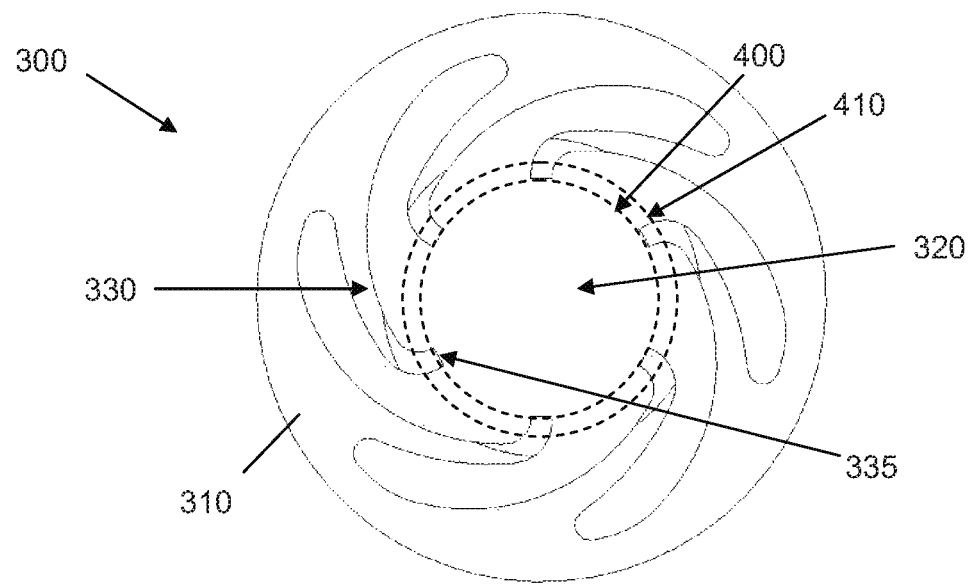

As shown in FIG. 8F, the lead contacting portions 335 of deflectable elements 300, in a relaxed state, are located along a circumference of an imaginary circle 400 concentric with the tubular body 310. The imaginary circle 400 has a diameter that is smaller than the outer diameter of the portion of the lead that the lead contact portions 335 are configured to contact. As the lead is inserted, the elements 330 deflect outwardly (relative to axial center of contact ring 300) to accommodate insertion of the lead. The resilient nature of the deflectable elements 330 biases the contacting portions 335 toward the circumference of the imaginary circle 400, forcing the contacting portions 335 against the inserted lead. Of course, if the contact of the lead, with which the lead contacting portions 335 are configured to contact, have an exterior shape different from a cylinder (e,g, cuboid), the lead contacting portions 335 may be configured to located along an imaginary shape (e.g., rectangle) similar in shape to the contact of the lead.

In the representative embodiments shown in FIGS. 8A-F, contact rings 300 include stops 340 configured to engage a stop portions 332 of elements 330 when the elements are sufficiently outwardly deflected. The stops 340 and stop portions 332 of elements 330 cooperate to inhibit outward deflection of the elements 330 when the stops 340 engage the stop portions 332. The cooperation of the stops 340 and the stop portions 332 inhibits damage to the elements 332; e.g. when a lead is placed into cavity 320 at an undesirable or unintended angle. In various embodiments, tubular body portion 310 of contact ring 300 forms stops 340 (see, e.g., FIGS. 8A and 8B). In numerous embodiments, deflectable elements 330 form stops 340 (see, e.g., FIGS. 8C-D). Any portion of the connector ring 300 that a deflectable element 330 contacts when outwardly deflected serves as a stop 340 provided that further outward deflection is inhibited or prevented. The portion of the element that contacts the stop 340 is the stop portion 332 of the element. As shown in, for example, the embodiments depicted in FIG. 8A the stop region 332 of the deflectable element 330 is a concave portion of the element 330. In the embodiment depicted in FIG. 8B, the deflectable elements 330 include a proximal portion 337 continuous with the tubular body 310 and a distal portion 339 extending inwardly from the tubular body 310. In the embodiment depicted in FIG. 8B, distal portion 339 includes the lead contacting portion 335 and forms the stop region 332. In the embodiment depicted in FIG. 8B, the stop region 332 includes a bulge of increased thickness relative to a region of the element 330 proximal to the stop region 332.

The deflecting elements 330 shown in FIGS. 8A and 8C-F are arcuate or substantially arcuate. The deflected elements may be generally linear, e.g. as shown in FIG. 8B. However, it will be understood that deflecting elements 330 may be of any suitable shape.

Referring now to FIG. 8E-F, by way of example, the deflectable elements may have a tapered region 334 in proximity to, adjacent to, or leading to, lead contacting portion 335. The tapered region 334 may serve as a ramp to facilitate insertion of the lead into the cavity of the connector ring. The tapered portion 334 preferably begins at a point on the elements proximal to where contact with the lead is expected. For example, the proximal beginning point of the tapered region 334 may begin on element 330 at a location along the circumference of an imaginary circle 410 coaxial with the tubular body portion 310 of the ring 300. The imaginary circle 410 has a diameter that is greater than the diameter of the portion of the lead that contacts the elements 330 as the lead is inserted into the contact ring 300. In the depicted embodiment, the distal ending point of the taper 334 is at the lead contact region 335 of the deflectable element 330, which lead contacting region 334 is disposed in the interior on the contact ring 300.

As the lead is inserted into the cavity in a direction from the proximal face 350 to the distal face of the connector, the lead can contact the tapered portion 334 causing the element 330 to deflect outwardly. Element 334 is torsionally biased towards a state where lead contacting portion 335 is located along a circumference of an imaginary circle 400 concentric with the tubular body 310. As described above with regard to FIG. 8F, the imaginary circle 400 has a diameter that is smaller than the outer diameter of the portion of the lead that the lead contact portions 335 are configured to contact.

The contact rings described herein may be formed from any suitable conductive material or materials. For example, the contact rings may be formed from platinum, platinum iridium, titanium, tantalum, palladium or alloys thereof nickel-cobalt-molybdenum alloys (such as MP35N); or the like; or combinations thereof. It will be understood that the material selected may vary on the ultimate design configuration. Generally, the elastic modulus or modulus of resiliency will be taken into account along with the design configuration, such as position and shape of stops and stop regions of the deflectable elements and the shape of the deflectable element, to minimize the stress and potential failure of the proximal portion of the deflectable element associated with insertion of a lead at an unintended angle.

In various embodiments, the contact rings are made of a core material having suitable modulus properties such as platinum, platinum iridium, titanium, tantalum, palladium or alloys thereof, or nickel-cobalt-molybdenum alloys. The core material may be plated, coated, clad, or the like with a softer material that is highly conductive, such as gold or the like. In some embodiments, a core of a less noble metal is plated, coated, clad, or the like with platinum, platinum iridium, titanium, tantalum, palladium or alloys thereof, or nickel-cobalt-molybdenum alloys.

In various embodiments, the contact rings are monolithic (formed from a single material without joints). Such monolithic contact rings (which can be of any suitable size, e.g. as described above) may improve the electrical properties of the contact ring relative to other contact rings, which employ a variety of materials or which require welding or other coupling between parts. By employing the same seamless material throughout, electrical resistance due to flow of electrons between the junctions of differing materials can be reduced, which can advantageously reduce the power requirement of devices employing the contact rings.

Contact rings 300 as described herein may be of any suitable size for use in implantable medical devices. For example, the contact rings 300 may have a thickness (axial length) between about 0.10 inches (2.5 millimeters) and about 0.01 inches (0.25 millimeters). In some embodiments, the contact rings 300 have a thickness of between about 0.75 inches (2 millimeters) and about 0.025 inches (0.6 millimeters); e.g., about 0.05 inches (1.2 millimeters). In numerous embodiments, contact rings 300 have a thickness that is approximately the same as the thickness of a ring contact of a lead to which the contact ring 300 is to be electrically coupled. The contact rings 300 may be of any suitable inner and outer diameter. For example, the contact rings 300 may have an outer diameter of between about 0.200 inches (5 millimeters) and 0.05 inches (1.2 millimeters). In some embodiments, the contact rings 300 have an outer diameter of about 0.1 inches (2.5 millimeters) or about 0.11 inches (2.8 millimeters). Generally, the inner diameter of the contact rings 300 (or the diameter formed by lead contacting portions 335 of the deflectable elements 330) is suitable for insertion of a lead. The deflectable elements 330 of the contact rings 300 may have any suitable length and thickness, which may vary depending on the material from which they are formed. The length will vary depending on the outer diameter of the ring and desired inner diameter formed from lead contacting portions 335 of the deflectable elements 330. In various embodiments, the deflectable elements 330 may have a thickness of between about 0.01 inches (0.25 millimeters) and about 0.001 inches (0.025 millimeters). In some embodiments, the deflectable elements 330 may have a thickness of between about 0.006 inches (0.15 millimeters) and about 0.002 inches (0.05 millimeters). The thickness of the deflectable elements 330 may be substantially the same along the length of the element or may vary along the length of the element. In some embodiments, the element 330 is thicker at the base and thinner at the lead contacting portion 335.

It will be understood that a contact ring 300 may include any suitable number of deflectable elements 330. For example, a contact ring may have between 1 and 100 or more deflectable elements. In some embodiments, the contact ring has between 3 and 6 or between 4 and 5 deflectable elements. All other thing being equal, the smaller the number of deflectable elements, the less force required to insert a lead through the cavity of the contact ring. However, if the insertion force is too low, the quality of electrical contact between the lead and the contacting portions of the deflectable elements may be poor. That is, greater resilient force pressing against the lead may lead to better quality and more reliable electrical contact, but may also result in greater insertion force. The number of deflectable elements included in a ring contact may be varied to achieve a desirable balance between quality and reliability of electrical contact and insertion force.

In addition, it may be desirable to decrease the number of contact points between the lead and the contact ring, as each point of contact may incrementally increase electrical resistance. Thus, in some embodiments, the lowest number of deflectable element that can provide high quality and reliable electrical contact with the lead is employed.

In some embodiments (not shown), at least a portion of the region between tubular body 310 and the lead contacting portions 335 of the deflectable elements 330 is backfilled with an elastomeric material, such as silicone. Such backfilling may increase the structural integrity and resilience of the elements 330, serving to reduce breakage.

Figure 9:
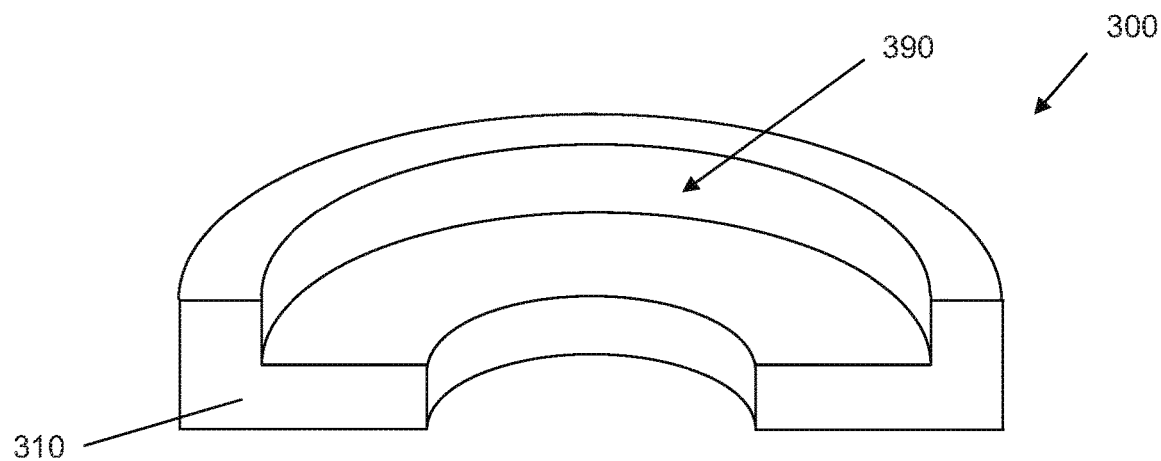
FIGS. 9-10 are schematic drawings of perspective views of sections of embodiments of contact rings having a flange for mating with a seal.
Figure 10:
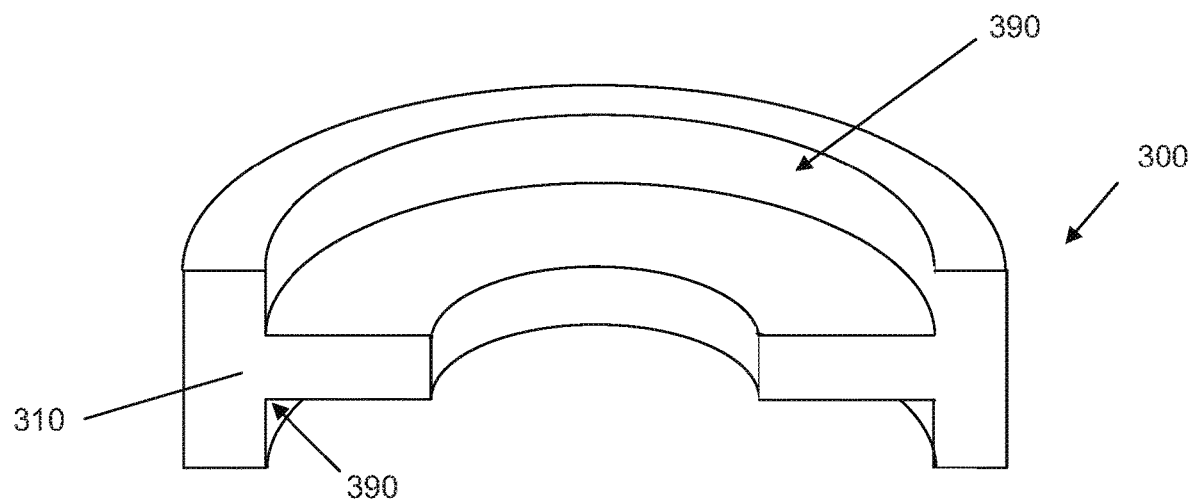

Referring now to FIGS. 9-10 in which schematic perspective views of sections of contact rings 300 are shown (shown without deflectable elements for purposes of convenience), the tubular body 310 of the contact ring 300 may form a flange 390 or rim configured to cooperate with an insulating seal when the contacts are used to form a lead receptacle (see e.g., FIGS. 5D-E). The contact ring 300 may have one flange region 390 (FIG. 9) or two flange regions 390 (FIG. 10) on opposing sides of the tubular body, allowing for sealing engagement with an insulating element on opposing sides of contact ring 300.

Contact rings 300 as described herein may be formed by any suitable process. For example, various components may be molded (e.g., microinjection molding), machined, or otherwise formed. In various embodiments, contact rings are formed by removing a solid portion of a cylinder to form the ring contact.

Figure 11A:
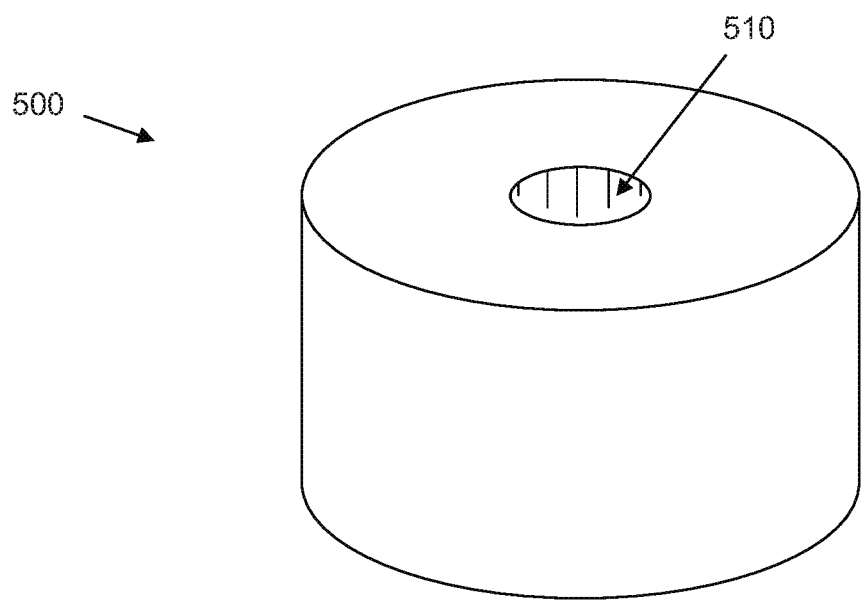
FIGS. 11A-D are schematic drawings of perspective views depicting removal of portions of a solid tubular material to generate a one-piece contact ring.
Figure 11B:
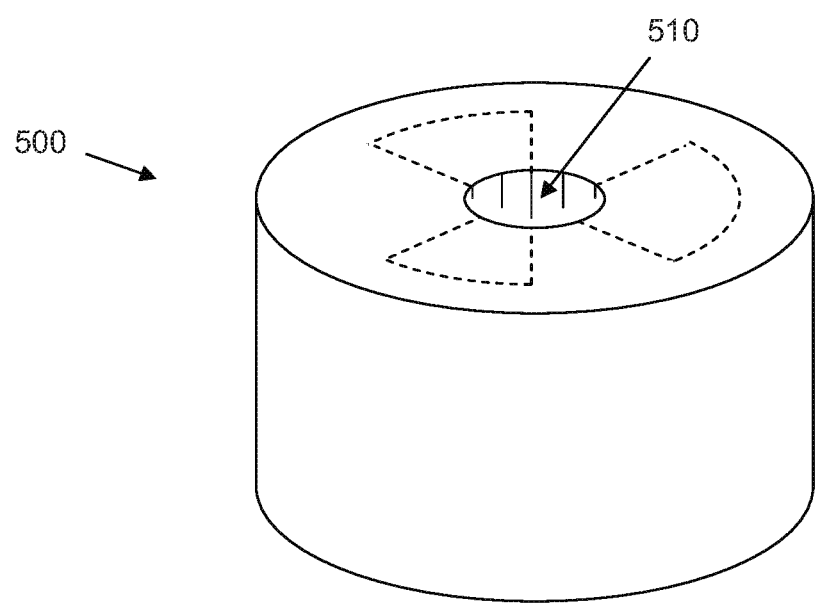
Figure 11C:
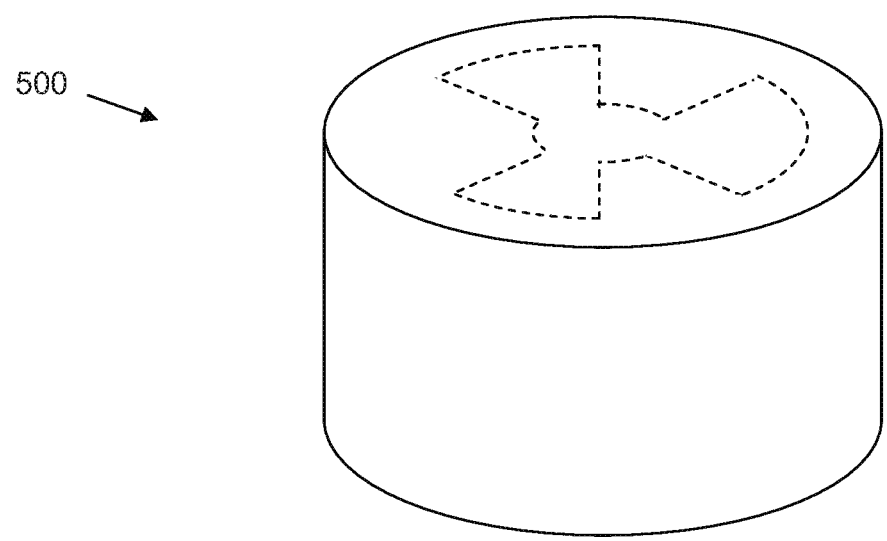

Referring now to FIGS. 11A-D, perspective views of representative cylinders 500 (FIG. 7A-C) that may serve as starting material for a contact ring 300 (FIG. 7D) by removal of a portion of the cylinder 500 (dashed lines in FIGS. 11B-C represent material to be removed). Any suitable method may be used to remove appropriate portion(s) of the cylinder 500. For example, electrical discharge machining, laser cutting, water jet cutting, photo-etching, or the like may be used to remove appropriate portion(s) of the cylinder 500. One example of electrical discharge machining that may be employed is wire electrical discharge machining; e.g., with a 0.004 inch wire. As shown in FIGS. 11A-B, the cylinder starting material may include a central cavity 510. It may be desirable for the diameter of the central cavity 510 to be the same as the diameter of the imaginary tube (see dashed line 400 in, e.g., FIG. 6F) along whose circumference the lead contacting portions of the deflectable elements lie in a relaxed state. Alternatively, the starting cylinder 500 may be solid throughout as shown in FIG. 11C.

Figure 11D:
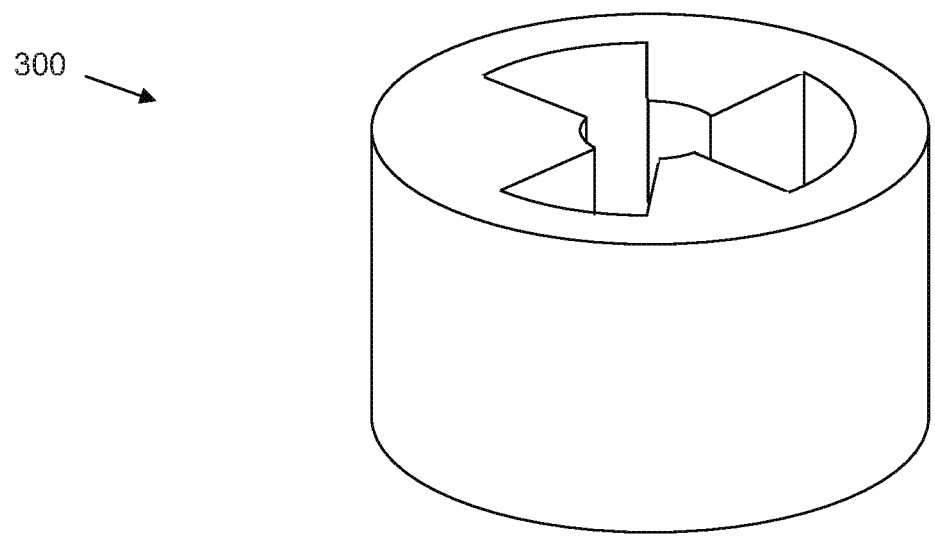
Figure 12:
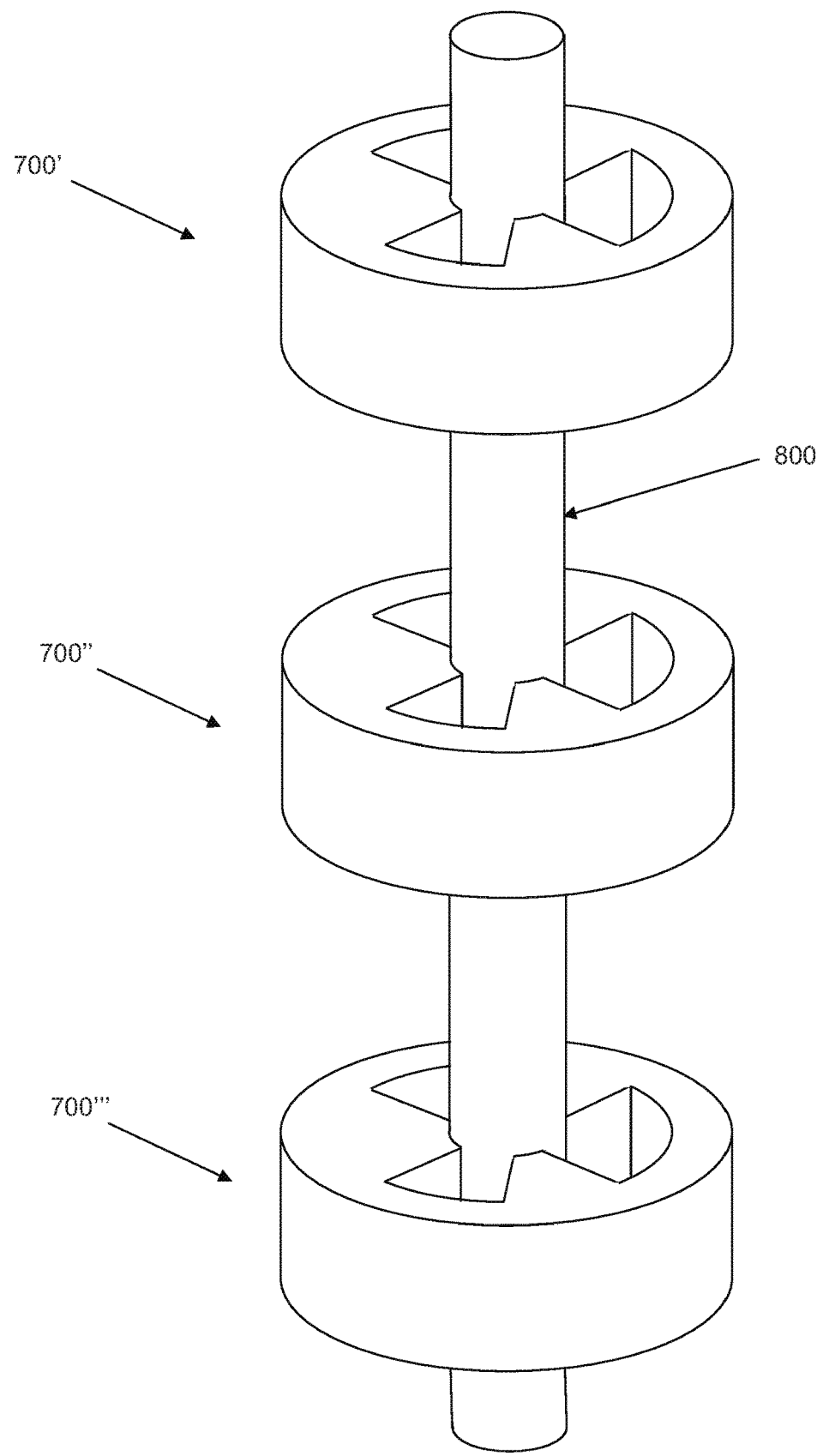
FIG. 12 is a schematic drawing of subunits of an electrical contact ring disposed about a mandrel.

Referring now to FIG. 12, a plurality of thin subunits 700', 700", 700"' may be axially aligned in a stacked manner and bonded to form a one-piece contact ring 300 (see, e.g., FIG. 11D). In the depicted embodiment, each subunit 700 includes a thinner version of all of the components of the connector ring. For example, each subunit includes a tubular body defining a cavity extending through the subunit body, a plurality of non-radially, outwardly deflectable subunit elements extending inwardly from the subunit tubular body, a plurality of subunit stops (see e.g., FIGS. 8A-F and associated text for a detailed description of such parts). The subunits 700', 700", 700"' may be axially aligned by placing the subunits 700', 700", 700"' about a mandrel 800. The subunits are brought into contact and the subunit tubular bodies, deflectable elements, and stops are aligned. Then adjacent stacked subunits are bonded to each other to form the one-piece electrical ring contact that may be used in an implantable medical device. Any suitable method for bonding, such as welding, may be employed.

The rings and cylinders depicted in FIGS. 11-12 are shown for the purposes of illustration only. It will be understood that rings having non-radially outwardly deflecting elements, such as those shown in FIGS. 8A-F may be made in a manner as described with regard to FIGS. 11-12.

The rings and cylinders depicted in the figures are shown for the purposes of illustration. It will be understood that the rings may take any suitable shape including cuboid or the like.

Thus, embodiments of the ELECTRICAL CONTACT FOR IMPLANTABLE MEDICAL DEVICE are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method for forming an electrical ring contact, comprising:
   forming plurality of thin subunits, each subunit having:
   (i) a subunit tubular body defining a cavity extending through the subunit body, and
   (ii) a plurality of resiliently deflectable subunit elements extending from the subunit tubular body into the cavity,
   axially aligning, in a stacked manner, the subunit tubular bodies and deflectable subunit elements; and
   bonding adjacent stacked subunits to each other to form the electrical ring contact.

2. The method of claim 1, wherein bonding the adjacent stacked subunits comprises welding the adjacent stacked subunits.

3. The method of claim 2, wherein axially aligning the subunits comprises disposing the subunits about a mandrel.

4. The method of claim 1, wherein the tubular body is formed from a material comprising a metal selected from the group consisting of platinum, platinum iridium, titanium, tantalum, palladium, or alloys thereof, and a nickel-cobalt-molybdenum alloy.

5. The method of claim 1, wherein plurality of resiliently deflectable subunit elements are arcuate.

6. The method of claim 1, wherein plurality of resiliently deflectable subunit elements comprise a tapered region in proximity to the lead contacting portion to facilitate insertion of the lead into the cavity.

7. The method of claim 1, wherein plurality of resiliently deflectable subunit elements consists of between 3 and 6 deflectable elements.

8. The method of claim 1, wherein plurality of resiliently deflectable subunit elements consists of 4 or 5 deflectable elements.

* * * * *